United States Patent
Zhao et al.

(10) Patent No.: US 10,126,244 B2
(45) Date of Patent: *Nov. 13, 2018

(54) APPARATUSES AND METHODS FOR PERFORMING SPECTROSCOPIC ANALYSIS OF A SUBJECT

(71) Applicant: B&W TEK LLC, Newark, DE (US)

(72) Inventors: Jun Zhao, The Woodlands, TX (US); Xin Jack Zhou, Hockessin, DE (US); Sean Xiaolu Wang, Wilmington, DE (US)

(73) Assignee: B&W TEK LLC, Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/461,613

(22) Filed: Mar. 17, 2017

(65) Prior Publication Data

US 2018/0136133 A1 May 17, 2018

Related U.S. Application Data

(63) Continuation-in-part of application No. 15/378,156, filed on Dec. 14, 2016, which is a continuation-in-part of application No. 15/349,510, filed on Nov. 11, 2016.

(51) Int. Cl.
*G01N 21/65* (2006.01)
*G01J 3/02* (2006.01)
(Continued)

(52) U.S. Cl.
CPC ............ *G01N 21/65* (2013.01); *G01J 3/0216* (2013.01); *G01J 3/0218* (2013.01); *G01J 3/4406* (2013.01);
(Continued)

(58) Field of Classification Search
CPC ............ G01N 21/65; G01N 2021/656; G01N 2201/068; G01N 2201/08; G01J 3/0216; G01J 3/44–2003/4424
(Continued)

(56) References Cited

U.S. PATENT DOCUMENTS 4,076,421 A    2/1978   Kishner
4,378,159 A * 3/1983   Galbraith ........... G01N 21/8901
                                               356/236
(Continued)

FOREIGN PATENT DOCUMENTS

DE    26 06 675     9/1977
DE    32 23 876     1/1983
(Continued)

OTHER PUBLICATIONS

English-language translation of German Office Action of German Application No. 102016225808.7, dated Nov. 24, 2017.

*Primary Examiner* — Michael P Lapage
(74) *Attorney, Agent, or Firm* — Blank Rome LLP

(57) ABSTRACT

This invention relates to a light delivery and collection device for performing spectroscopic analysis of a subject. The light delivery and collection device comprises a reflective cavity with two apertures. The first aperture is configured to receive excitation light which then diverges and projects onto the second aperture. The second aperture is configured to be applied close to the subject such that the reflective cavity substantially forms an enclosure covering a large area of the subject. The excitation light enters and interacts with the covered area of the subject to produce inelastic scattering and/or fluorescence emission from the subject. The reflective cavity has a specular reflective surface with high reflectivity to the excitation light as well as to the inelastic scattering and/or fluorescence emission from the subject. The reflective cavity reflects the excitation light (Continued)

that is reflected and/or back-scattered from the subject and redirects it towards the subject. This causes more excitation light to penetrate into a diffusely scattering subject to produce inelastic scattering and/or fluorescence emission from inside of the subject hence enabling sub-surface measurement. In addition, the reflective cavity reflects the inelastic scattering and/or fluorescence emission from the subject unless the inelastic scattering and/or fluorescence emission either emits from the first aperture of the reflective cavity to be measured with a spectrometer device, or re-enters the subject at the second aperture. This multi-reflection process improves the collection efficiency of the inelastic scattering or fluorescence emission from the subject.

21 Claims, 12 Drawing Sheets

(51) Int. Cl.
*G01J 3/44* (2006.01)
*G01N 21/47* (2006.01)
*G01N 21/64* (2006.01)

(52) U.S. Cl.
CPC ......... *G01N 21/474* (2013.01); *G01N 21/645* (2013.01); *G01N 2201/064* (2013.01); *G01N 2201/08* (2013.01)

(58) Field of Classification Search
USPC ........................................................ 356/445
See application file for complete search history.

(56) References Cited

U.S. PATENT DOCUMENTS

| | | |
|---|---|---|
| 4,645,340 A | 2/1987 | Graham et al. |
| 4,853,542 A | 8/1989 | Milosevic et al. |
| 4,988,205 A | 1/1991 | Snail |
| 5,112,127 A * | 5/1992 | Carrabba .................. G01J 3/44 250/227.23 |
| 5,199,431 A * | 4/1993 | Kittrell .............. A61B 1/00096 600/476 |
| 5,280,788 A * | 1/1994 | Janes .................. A61B 5/0084 600/476 |
| 5,517,315 A * | 5/1996 | Snail .................... G01N 21/474 250/339.07 |
| 5,615,673 A * | 4/1997 | Berger ............... A61B 5/14532 356/301 |
| 5,659,397 A | 8/1997 | Miller et al. |
| 5,864,397 A * | 1/1999 | Vo-Dinh .................. G01J 3/44 356/301 |
| 6,370,406 B1 * | 4/2002 | Wach .................. G01N 21/474 356/301 |
| 6,781,697 B1 * | 8/2004 | Carra ..................... G01N 21/57 356/236 |
| 7,148,963 B2 | 12/2006 | Owen et al. |
| 7,652,763 B2 | 1/2010 | Matousek et al. |
| 7,671,985 B1 * | 3/2010 | Milosevic ............ G01N 21/474 356/301 |
| 8,248,600 B2 | 8/2012 | Matousek et al. |
| 2004/0263842 A1* | 12/2004 | Puppels ................. G01N 21/65 356/301 |
| 2012/0089030 A1* | 4/2012 | Guze ................... A61B 5/0088 600/476 |
| 2013/0038869 A1 | 2/2013 | Lascola et al. |
| 2016/0209388 A1 | 7/2016 | Yakovlev et al. |

FOREIGN PATENT DOCUMENTS

| | | |
|---|---|---|
| DE | 33 11 954 | 2/1992 |
| DE | 693 13 633 | 4/1998 |
| DE | 11 2006 000 273 | 1/2013 |
| DE | 10 2012 101 744 | 9/2013 |
| WO | WO-98/22802 | 5/1998 |
| WO | 2004/031749 A2 | 4/2004 |
| WO | WO-2015/114379 | 8/2015 |

* cited by examiner

Raman Shift (cm-1)

Raman Shift (cm-1)

Raman Shift (cm-1)

APPARATUSES AND METHODS FOR PERFORMING SPECTROSCOPIC ANALYSIS OF A SUBJECT

REFERENCE TO RELATED APPLICATION

This application is a continuation-in-part of U.S. application Ser. No. 15/378,156, entitled "LIGHT DELIVERY AND COLLECTION DEVICE FOR MEASURING RAMAN SCATTERING OF A SAMPLE", filed on Dec. 14, 2016, by Jun Zhao, Xin Jack Zhou, and Sean Xiaolu Wang, which is a continuation-in-part of U.S. application Ser. No. 15/349,510, entitled "LIGHT DELIVERY AND COLLECTION DEVICE FOR MEASURING RAMAN SCATTERING OF A SAMPLE", filed on Nov. 11, 2016, by Jun Zhao and Xin Jack Zhou. The subject matter of the aforementioned U.S. applications is hereby incorporated herein by reference.

FIELD OF THE INVENTION

This invention generally relates to a light delivery and collection device, and more specifically to a light delivery and collection device for performing spectroscopic analysis of a subject.

BACKGROUND

Optical spectroscopy measures the interaction of light, especially monochromatic light with a material to produce a spectrum characteristic of the material. Such interaction includes inelastic scattering processes, such as Raman and Brillouin scattering, and fluorescence emission process. Optical spectroscopy has been demonstrated to be a powerful non-invasive analytical technology for material characterization and identification.

Conventional optical spectroscopy generally utilizes a well-focused laser beam to produce inelastic scattering and/or fluorescence signal from the sample. This approach has the apparent advantage of relatively high efficiency in signal excitation and collection. However, it also suffers from the following drawbacks. First, only a small volume of the sample is measured. Thus the collected optical spectra may not be very representative, especially for some non-uniform samples. Second, the tightly focused laser beam may cause damage to some delicate samples. Third, for diffusely scattering samples which are not transparent to the laser beam, this approach will only measure the inelastic scattering and/or fluorescence signal from the surface layer of the sample. The majority of the material underneath the surface will be almost completely out of reach.

There thus exists a need for an improved light delivery and collection device for performing optical spectroscopy, which not only allows the measurement of a large area of the sample but also enables sub-surface optical signal excitation and collection.

SUMMARY OF THE INVENTION

It is the object of the present invention to provide a light delivery and collection device for performing spectroscopic analysis of a subject. The light delivery and collection device comprises a reflective cavity with two apertures. The first aperture is configured to receive excitation light which then diverges and projects onto the second aperture. The second aperture is configured to be applied close to the subject such that the reflective cavity substantially forms an enclosure covering a large area of the subject. The excitation light enters and interacts with the covered area of the subject to produce inelastic scattering and/or fluorescence emission from the subject. The reflective cavity has a specular reflective surface with high reflectivity to the excitation light as well as to the inelastic scattering and/or fluorescence emission from the subject. The reflective cavity reflects the excitation light that is reflected and/or back-scattered from the subject and redirects it towards the subject. This causes more excitation light to penetrate into a diffusely scattering subject to produce inelastic scattering and/or fluorescence emission from inside of the subject hence enabling sub-surface measurement. In addition, the reflective cavity reflects the inelastic scattering and/or fluorescence emission from the subject unless the inelastic scattering and/or fluorescence emission either emits from the first aperture of the reflective cavity to be measured with a spectrometer device, or re-enters the subject at the second aperture. This multi-reflection process improves the collection efficiency of the inelastic scattering and/or fluorescence emission from the subject.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1A:
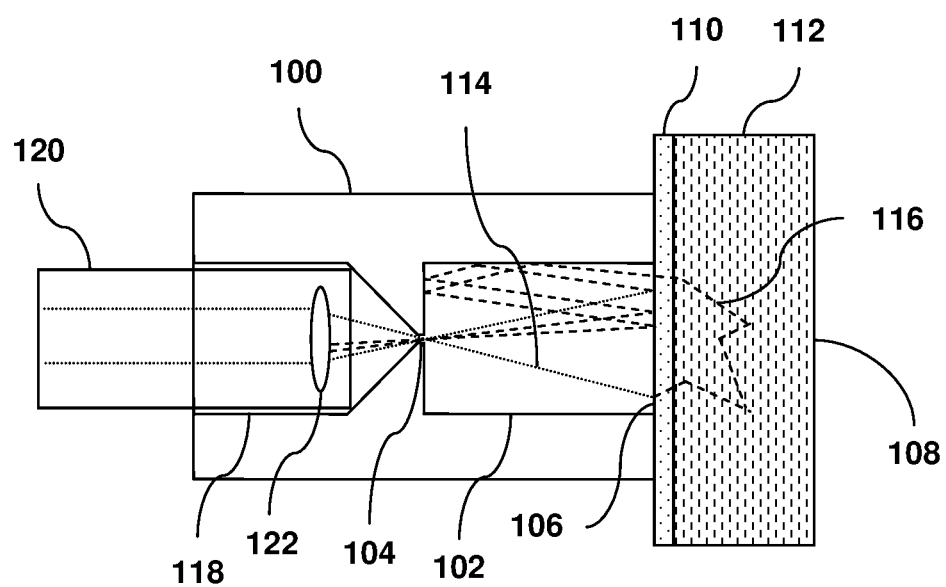
FIG. 1A-C illustrates a first exemplary embodiment of the light delivery and collection device having a reflective cavity for Raman scattering excitation and collection as well as a receptacle for receiving a probe.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a light delivery and collection device for performing spectroscopic analysis of a subject. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1A illustrates a first exemplary embodiment of the light delivery and collection device, which is configured to deliver excitation light to a large area of a sample and collect the Raman scattered light generated thereof. The light delivery and collection device 100 comprises a reflective cavity 102 which is made of a material having high reflectivity to the excitation light and the Raman scattered light. Such material can be metal materials, e.g. gold, silver, copper, and aluminum, etc. The surface of the reflective cavity is preferably polished to produce specular reflection to the excitation light and the Raman scattered light. Alternatively, the reflective cavity 102 may have a surface coating with high reflectivity to the excitation light and the Raman scattered light. Such surface coating can be a metal coating which exhibits high reflection in a broad range of wavelengths. Or it can be a dielectric coating, which has a customized reflection wavelength range. The latter one may reflect only the wavelengths of interest thus rejecting stray light which does not overlap with the excitation light and the Raman scattered light in wavelength. The surface coating is preferably a smooth coating to produce specular reflection to the excitation light and the Raman scattered light. The reflective cavity 102 may be made of a flexible material such that it can accommodate variously shaped sample surfaces.

The light delivery and collection device 100 further comprises a receptacle 118 which is configured to receive a probe 120. The probe 120 comprises one or more optical components 122, such as optical lenses, mirrors, filters, beam splitters, optical fibers, etc., which receive excitation light from a light source, such as a laser light source (not shown) and focus the excitation light at a first aperture 104 of the reflective cavity 102 and thereby deliver the excitation light 114 into the reflective cavity 102. The aperture 104 preferably has a size as small as possible, but large enough to pass unobstructed the excitation light and the Raman light collectable by the probe 120. The excitation light 114 diverges and projects onto a second aperture 106 of the reflective cavity 102, which preferably has a size much larger than the first aperture 104, and more preferably, at least two times as large as the first aperture 104 in area and covers an area of at least a few square millimeters. The second aperture 106 of the reflective cavity 102 is configured to be applied close to the sample 108 such that the reflective cavity 102 substantially forms an enclosure covering a large area of the sample 108, where the excitation light 114 enters and produces Raman scattered light 116 from the covered area of the sample 108. By collecting the Raman scattering from a large volume of the sample, the intensity of excitation light on the sample is reduced to avoid sample damage. In the meantime, the collected Raman spectrum is more representative, especially for non-uniform samples. Here the sample 108 can be diffusely scattering samples, such as pharmaceuticals, powders, biological tissues, etc. or even samples having multiple layers of different materials. In the example as shown in FIG. 1A, the sample 108 is a diffusely scattering sample having a surface layer 110 and a sub-surface layer 112, e.g. a container with powder samples inside. The sample 108 reflects and/or scatters the excitation light 114, either through elastic scattering or inelastic scattering (i.e. Raman scattering and Brillouin scattering) back into the reflective cavity 102. The reflective cavity 102 reflects the excitation light that is reflected and/or back-scattered from the sample and redirects it towards the sample. This causes more excitation light to penetrate into the diffusely scattering sample to produce Raman scattering from the sub-surface layer 112 of the sample 108. In addition, the reflective cavity 102 reflects the Raman scattered light from the sample unless the Raman scattered light either emits from the first aperture 104 to be collected by the probe 120 and then measured with a spectrometer device (not shown) to obtain a Raman spectrum of the sample 108, or re-enters the sample 108 and be re-scattered by the sample 108 at the second aperture 106. This multi-reflection process improves the collection efficiency of the Raman scattered light from the sample. In this example, the excitation light 114 penetrates through the surface layer 110 of the sample 108 with the aid of the reflective cavity 102 and produces Raman scattering from the sub-surface layer 112 of the sample 108. Hence the measured Raman spectrum contains the characteristic information of both the surface layer 110 and the sub-surface layer 112 of the sample 108. In a separate step, the light delivery and collection device 100 can be removed and the excitation light from the probe 120 is directly focused onto the surface layer 110 of the sample 108 to measure a Raman spectrum of the surface layer 110. The latter Raman spectrum can be mathematically extracted from the previously measured Raman spectrum to obtain a Raman spectrum of the sub-surface layer of the sample. The enhanced excitation and collection efficiency of the Raman scattered light as provided by the reflective cavity hence enables sub-surface Raman scattering measurement.

Figure 1B:
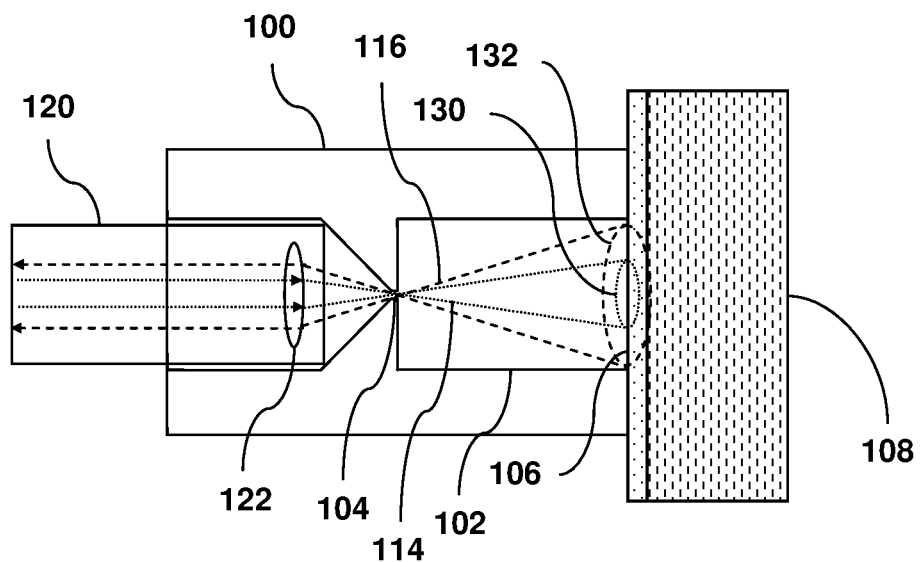
Figure 1C:
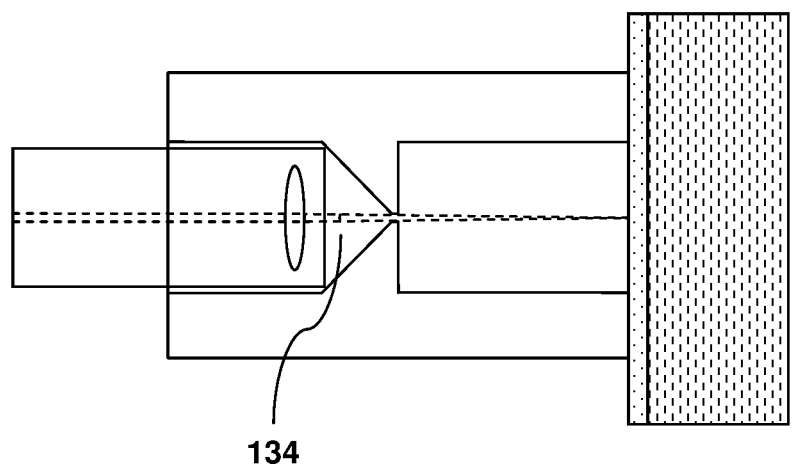

Optically, the reflective cavity serves three purposes, including (i) to provide a large sampling area; (ii) to maximize signal collection by means of multiple reflection and scattering as explained previously; and (iii) to isolate the sampled area from ambient light which would otherwise contaminate the signal. The size of the sampling area should be determined by the specific sampling requirement. For example, if the sample is heterogeneous and the goal is to obtain a better representation of the sample in whole, the sampling area should be made at least several times larger than the grain size of the sample. If the purpose is to measure sub-surface sample through a layer of packaging material, then the linear size of the sampling area should be several times the thickness of the packaging material. With the desired sampling area determined, FIG. 1B and FIG. 1C further illustrate the design considerations of the reflective cavity to achieve maximum signal collection. Referring to FIG. 1B, the excitation light beam 114 from the probe 120 is focused by the optical components 122 at the first aperture 104, and then diverges and projects onto the second aperture 106, covering an initial illumination area 130. The light beam 116 collectable by the probe optics similarly projects a collection area 132. The collection area 132 and the initial illumination area 130 may be different in size. With the probe optics fixed, the minimum size of the first aperture 104 and the divergence angles of both beams are determined. For maximum collection efficiency, the size of the first aperture 104 should be made as small as possible without obstructing the excitation and collection beams, that is, just large enough to encircle their beam waists at the first aperture 104. If it is made much larger, scattered excitation light and Raman light falling on the area outside the collection beam waist but inside the first aperture will exit the first aperture 104 without being collected by the probe 120. To determine the size of the second aperture 106 for maximum signal collection, one shall first consider that the light outside the aperture is blocked, so the aperture should be at least the size of the desired sampling area. Next, the inevitable loss at each reflection by the reflective cavity 102 and at each scattering by the sample 108 must be considered. For maximum collection efficiency, the Raman scattered light should be allowed to exit the first aperture 104 and to be collected by the probe 120 by going through as few rounds of reflection and scattering as possible. If the second aperture 106 is made larger than the projected area 132, Raman light emerging from the area outside the projected area 132 cannot be captured by the probe 120 without going through more reflection and scattering, which will result in reduced efficiency and limit the effective sampling area to area 132. Therefore the sampling area is the smaller of area 132 and the second aperture 106. On the other hand, the angle of collection 134 as shown in FIG. 1C for signal light from the second aperture 106 is proportional to the collection beam size at the first aperture 104 and inversely proportional to the cavity length. The larger this angle is, the higher the collection efficiency. Therefore, the cavity length should be made as short as possible, without reducing the projected area 132 to below the required sampling area. These factors combine to provide that for optimal efficiency, the size of the second aperture 106 should be equal to the desired sampling area, and that the cavity length should be such that the projected area 132 is equal to the size of the second aperture 106. Preferably, the second aperture 106 of the reflective cavity 102 is at least two times as large as the first aperture 104 in area.

Figure 2:
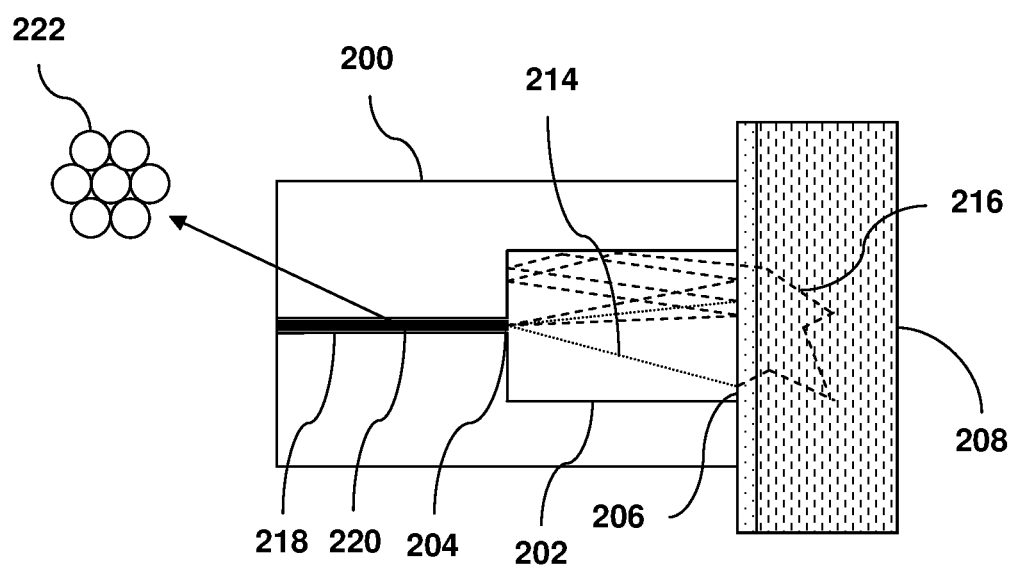
FIG. 2 illustrates a second exemplary embodiment of the light delivery and collection device having a reflective cavity for Raman scattering excitation and collection as well as a receptacle for receiving an optical fiber or fiber bundle.

FIG. 2 illustrates a second exemplary embodiment of the light delivery and collection device. Here the light delivery and collection device 200 comprises a reflective cavity 202 having a similar structure as the reflective cavity 102 in FIG. 1A, as well as a receptacle 218 which is configured to receive one or more optical fibers or fiber bundles 220. The optical fiber or fiber bundle terminates at the proximity of a first aperture 204 of the reflective cavity 202 so as to deliver the excitation light from a light source (not shown) into the reflective cavity 202. In a similar way as shown in FIG. 1A, the excitation light 214 excites Raman scattering from the sample 208 at a second aperture 206 of the reflective cavity 202. The reflective cavity 202 reflects the excitation light that is reflected and/or back-scattered from the sample and redirects it towards the sample. In addition, it reflects the Raman scattered light from the sample unless the Raman scattered light either emits from the first aperture 204 to be collected by the probe 220 and then measured with a spectrometer device (not shown) to obtain a Raman spectrum of the sample 208, or re-entered sample 208 and be re-scattered by the sample 208 at the second aperture 206. The fiber bundle 220 may comprise multiple optical fibers 222. A portion of the fibers, e.g. the fiber in the center of the bundle may be used for delivering the excitation light while the other portion of the fibers, e.g. the fibers at the periphery of the bundle may be used for collecting the Raman scattered light.

Figure 3:
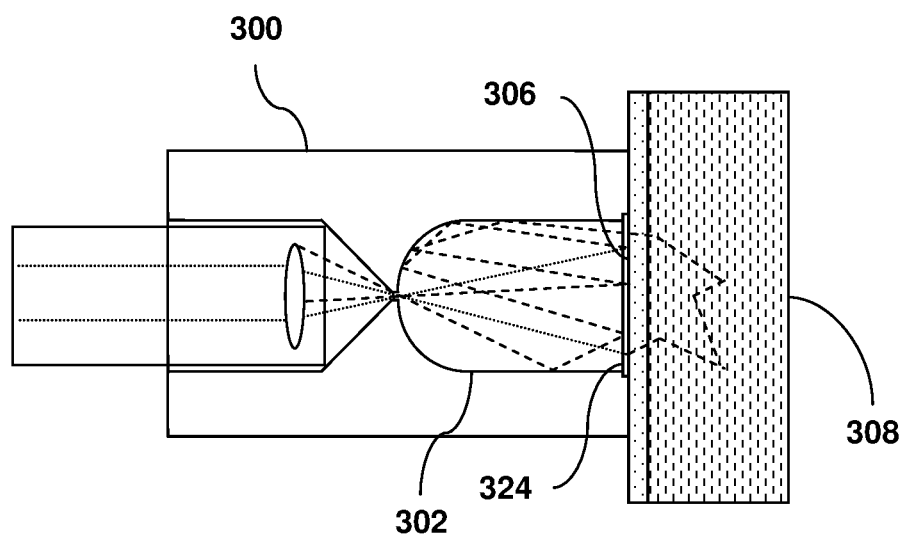
FIG. 3 illustrates a variation of the first exemplary embodiment of the light delivery and collection device, which has a differently shaped reflective cavity.

The reflective cavity of the light delivery and collection device may take different shapes, e.g. cylindrical shape, conical shape, spherical shape, or paraboloidal shape, etc. In a slight variation of the light delivery and collection device as shown in FIG. 3, the reflective cavity 302 of the light delivery and collection device 300 is spherically or paraboloidal shaped. The special shape may favorably reflect the light into certain directions hence increasing the excitation and collection efficiency of the Raman scattering in those directions. In addition, the reflective cavity 302 may comprise an optical window 324 covering its second aperture 306, thus preventing the surface of the cavity from possible contamination from the sample 308. The optical window 324 can be a flexible membrane such that the second aperture 306 of the reflective cavity 302 can accommodate variously shaped sample surfaces. The optical window 324 is preferably transparent to the excitation light and the Raman scattered light, and the thickness of the optical window 324 should be thin enough to avoid causing excessive insertion loss to the excitation light and the Raman scattered light. By selecting an appropriate material for the optical window 324, it is also possible to utilize the Raman scattering from the optical window as a reference for calibrating the wavelength (or Raman shift) of the measured Raman spectrum.

In yet another variation of the light delivery and collection device, the relative position of the first and second aperture of the reflective cavity may be adjusted. For example, the first aperture may be off-axis from the center of the second aperture such that the excitation light obliquely illuminates the sample. The reflective cavity may have an additional aperture for outputting the Raman scattered light. The position of this aperture on the reflective cavity may be optimized, for example, to minimize the percentage of the collected Raman scattering signal from the surface material of the sample and maximize the percentage of the collected Raman scattering signal from the sub-surface material of the sample. Alternatively, the additional aperture may be used to deliver another excitation light of different wavelength to excite Raman scattering from the sample. In addition, the reflective cavity may be filled with an optical medium, such as a gas or liquid medium, for modifying the optical property of the excitation light and the Raman light.

Figure 4:
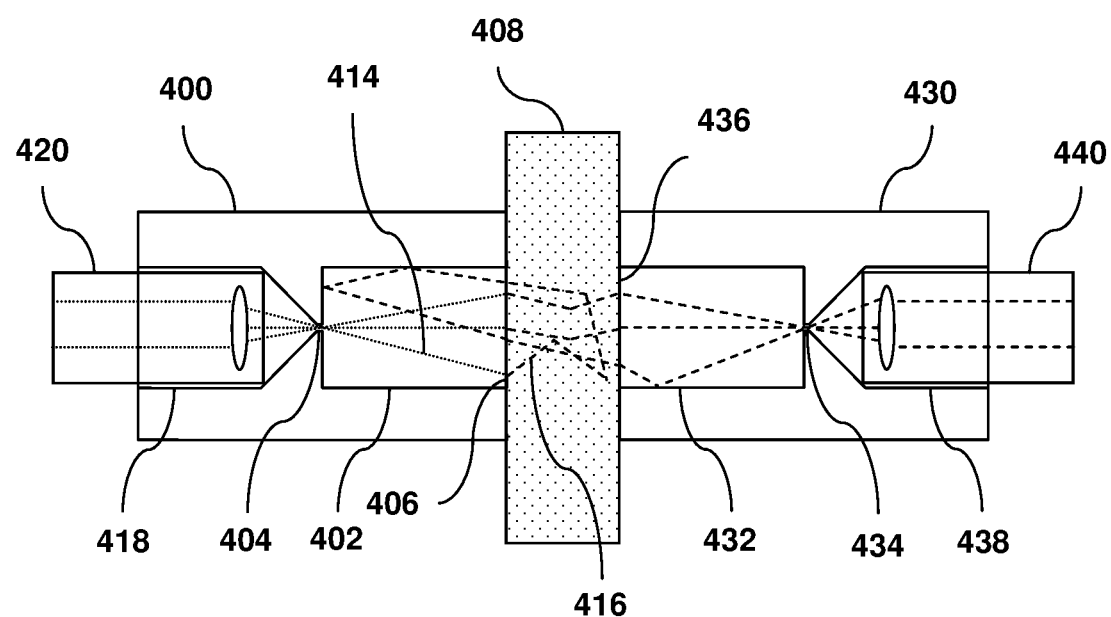
FIG. 4 illustrates a scheme of utilizing the first exemplary embodiment of the light delivery and collection device for measuring the transmissive Raman scattering of a diffusely scattering sample.

FIG. 4 illustrates a scheme of utilizing the first exemplary embodiment of the light delivery and collection device for measuring the transmissive Raman scattering of a diffusely scattering sample. In this example, two of such devices are utilized. One device is used for delivering the excitation light to one side of the sample, and another device is used for collecting the Raman scattered light from the opposite side of the sample. Referring to FIG. 4, the light delivery device 400 has a receptacle 418 to receive a probe 420 and a reflective cavity 402 with its first aperture 404 in communication with the probe 420 to receive the excitation light 414. The second aperture 406 of the light delivery device 400 is applied close to one side of the sample 408 such that the reflective cavity 402 of the light delivery device 400 substantially forms an enclosure covering a large area of the sample to excite Raman scattered light 416 thereof. The light collection device 430 has a reflective cavity 432 with its second aperture 436 applied onto the opposite side of the sample 408 such that the reflective cavity 432 collects the Raman scattered light that transmits through the sample 408 and delivers it through the first aperture 434 of the reflective cavity 432 to a probe 440 in a receptacle 438 to be analyzed by a spectrometer device (not shown). The reflective cavity 402 of the light delivery device 400 enhances the Raman excitation and collection efficiency by reflecting back into the sample the majority of excitation light and Raman scattered light that are reflected and/or scattered back by the sample until they transmit through the sample. The reflective cavity 432 of the light delivery device 430 functions similarly by reflecting back the excitation light and Raman scattered light which do not fall on its exit aperture, i.e. the first aperture 434. In a slight variation of the present scheme, the light delivery device 400 may also be used for collecting the back scattered Raman light from the sample 408 in a similar way as shown in FIG. 1A. The spectra of the back scattered Raman light and the forward scattered Raman light may be used together to analyze the composition of the sample 408.

Figure 5:
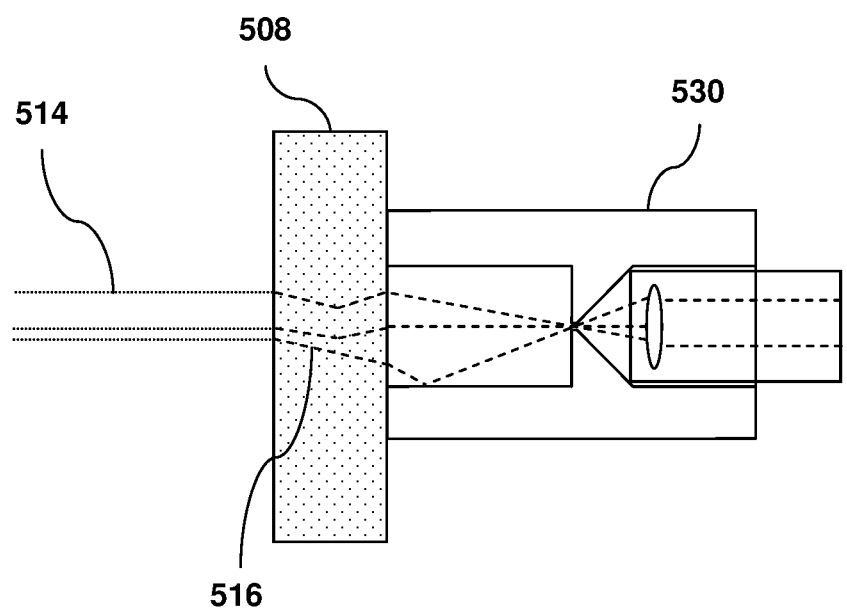
FIG. 5 illustrates a slightly different scheme of utilizing the first exemplary embodiment of the light delivery and collection device for measuring the transmissive Raman scattering of a diffusely scattering sample.

FIG. 5 illustrates a slightly different scheme of utilizing the first exemplary embodiment of the light delivery and collection device for measuring the transmissive Raman scattering of a diffusely scattering sample. Here the excitation light 514 is directly delivered onto one side of the sample 508 to excite Raman scattered light 516 from the sample. The excitation light 514 can be either collimated, or converging, or diverging. A light collection device 530 with a similar design as shown in FIG. 1A is employed to collect the Raman scattered light 516 that transmits through the sample 508.

In a similar manner, the light delivery and collection device as shown FIG. 2 and FIG. 3 may be used for measuring the transmissive Raman scattering of transparent or diffusely scattering samples.

Figure 6:
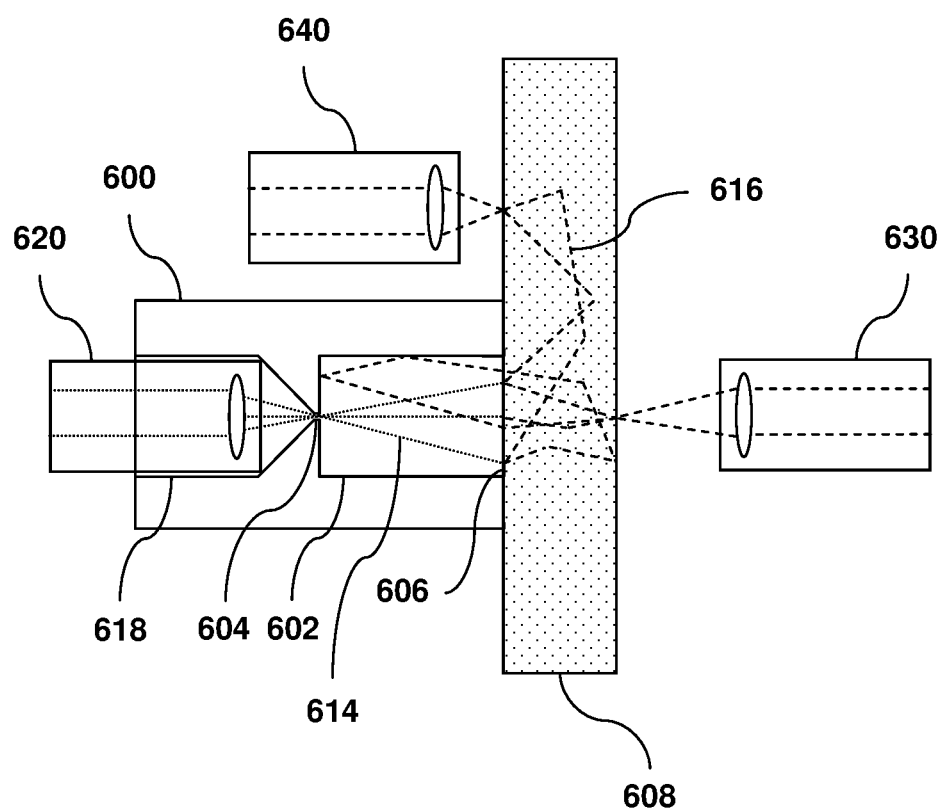
FIG. 6 illustrates another scheme of utilizing the first exemplary embodiment of the light delivery and collection device for measuring the Raman scattering of a diffusely scattering sample.

FIG. 6 illustrates another scheme of utilizing the first exemplary embodiment of the light delivery and collection device for measuring the Raman scattering of a diffusely scattering sample. In this scheme, the device is used for delivering the excitation light to the sample. Similar to the light delivery and collection device as shown in FIG. 1A, the light delivery device 600 has a receptacle 618 to receive a probe 620 and a reflective cavity 602 with its first aperture 604 in communication with the probe 620 to receive the excitation light 614. The second aperture 606 of the light delivery device 600 is applied close to the sample 608 such that the reflective cavity 602 of the light delivery device 600 substantially forms an enclosure covering a large area of the sample to excite Raman scattered light 616 thereof. The reflective cavity 602 reflects the excitation light that is reflected and/or back-scattered from the sample and redirects it towards the sample. This causes more excitation light to penetrate into the diffusely scattering sample to produce Raman scattering from inside of the sample. The Raman scattered light which transmits through the sample 608 is collected by a probe 630 and then delivered into a spectrometer device (not shown) for spectral analysis. The back-scattered Raman light is collected by another probe 640, which is placed adjacent to the light delivery device 600. In this scheme, the probe 630 and 640 can be conventional Raman probes with optical components designed to collect the Raman scattered light from a small area of the sample or they can have a similar structure as the light delivery and collection device in FIG. 1A, which is designed to collect the Raman scattered light from a large area of the sample. Alternatively, the conventional Raman probe 640 may be used for delivering the excitation light to the sample to excite Raman scattered light and the light delivery and collection device 600 may be used for collecting the Raman scattered light.

Figure 7:
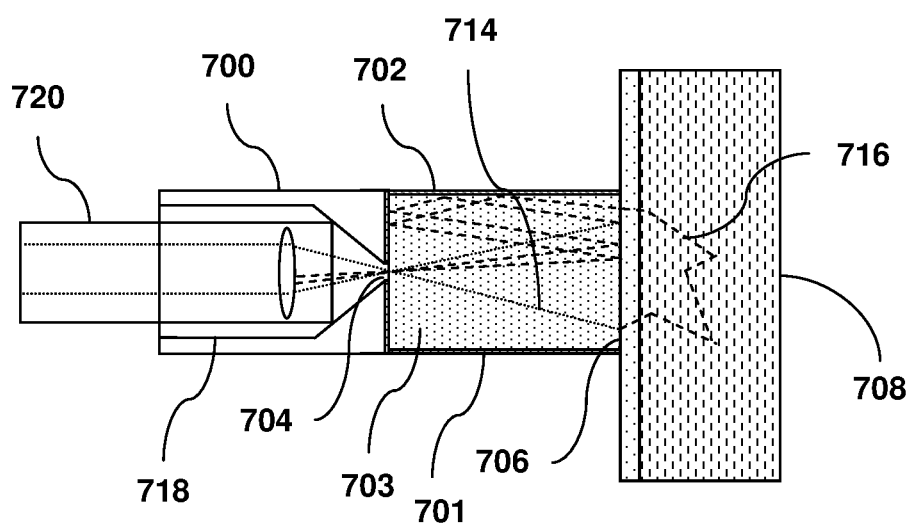
FIG. 7 illustrates a third exemplary embodiment of the light delivery and collection device, which has a reflective cavity that is formed by a solid optical material with a reflective coating.

FIG. 7 illustrates a third exemplary embodiment of the light delivery and collection device. Here the light delivery and collection device 700 comprises a reflective cavity 702 which is made of a solid optical material 703 with a reflective coating 701. The reflective coating 701 has two openings, which form the first aperture 704 and the second aperture 706 of the reflective cavity 702. The light delivery and collection device 700 further comprises a receptacle 718 which is configured to receive a probe 720. The probe 720 receives excitation light from a light source and focuses the excitation light at the first aperture 704 of the reflective cavity 702 and thereby delivers the excitation light 714 into the reflective cavity 702. In a similar way as shown in FIG. 1A, the excitation light 714 excites Raman scattering from the sample 708 at the second aperture 706 of the reflective cavity 702. The reflective cavity 702 reflects the excitation light that is reflected and/or back-scattered from the sample and redirects it towards the sample. In addition, it reflects the Raman scattered light from the sample unless the Raman scattered light either emits from the first aperture 704 to be collected by the probe 720 and then measured with a spectrometer device (not shown) to obtain a Raman spectrum of the sample 708, or re-enters the sample 708 and be re-scattered by the sample 708 at the second aperture 706. The optical material 703 is preferably transparent to the excitation light 714 and the Raman scattered light 716. It may have a refractive index profile which is spatially heterogeneous, hence causing changes in the propagation direction of the excitation light and the Raman light. As one example, the optical material 603 may have a gradient-index (GRIN) profile with a parabolic variation of refractive index such that it functions as an optical lens. When the effective focal length of this GRIN lens is equal to the length of the reflective cavity 702, the excitation light 714 from the first aperture 704 will be collimated by the GRIN lens when it reaches the second aperture 706, which in turn increases the penetration depth of the excitation light into the sample 708.

Figure 8:
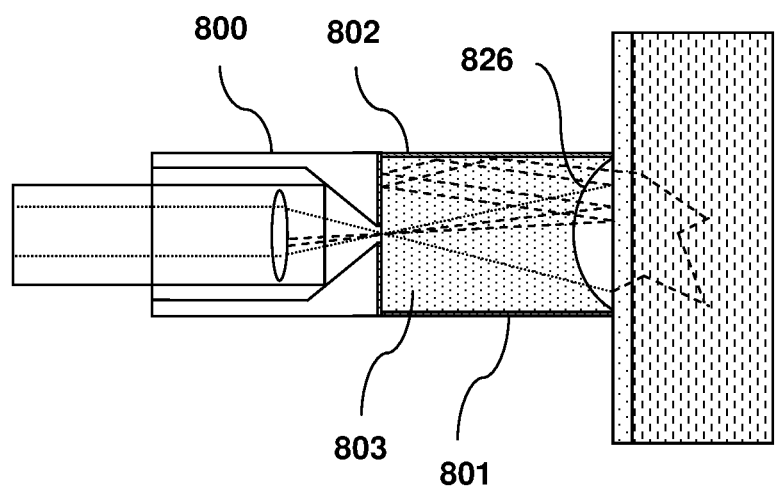
FIG. 8 illustrates a slight variation of the third exemplary embodiment of the light delivery and collection device.

FIG. 8 illustrates a slight variation of the third exemplary embodiment of the light delivery and collection device. In this variation, the light delivery and collection device 800 comprises a reflective cavity 802 which is made of a solid optical material 803 having a curved end surface 826. The end surface 826 and the other surfaces 801 of the optical material 803 may have reflective coatings reflecting at different wavelengths. As one example, the end surface 826 may reflect the excitation light and the other surfaces 801 may reflect the Raman light such that the excitation light and the Raman light are reflected by two differently shaped reflective cavities.

The light delivery and collection device as disclosed above may be utilized to improve the excitation and collection efficiency for a variety of spectroscopic measurements, including Raman spectroscopy and Brillouin spectroscopy, where a shift in wavelength of the inelastically scattered light provides the structural information of the subject sample, as well as fluorescence and phosphorescence spectroscopy, where the absorption of excitation light at a shorter wavelength and emission of fluorescent light at a longer wavelength reveals the electronic and vibrational state information of the subject sample.

FIG. 9 and FIG. 10 show two examples of utilizing the light delivery and collection device for measuring the Raman spectra of diffusely scattering samples contained inside diffusely scattering containers.

Figure 9A:
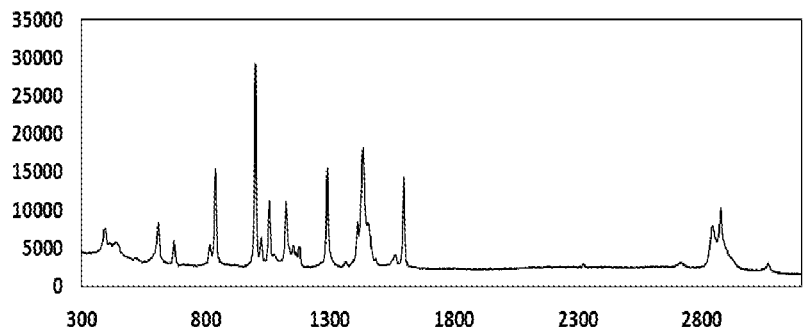
FIG. 9A-D shows the measured Raman spectrum of a sodium benzoate sample contained in a plastic bottle, as well as the Raman spectrum of the plastic bottle and the Raman spectrum of the sodium benzoate sample for comparison.
Figure 9B:
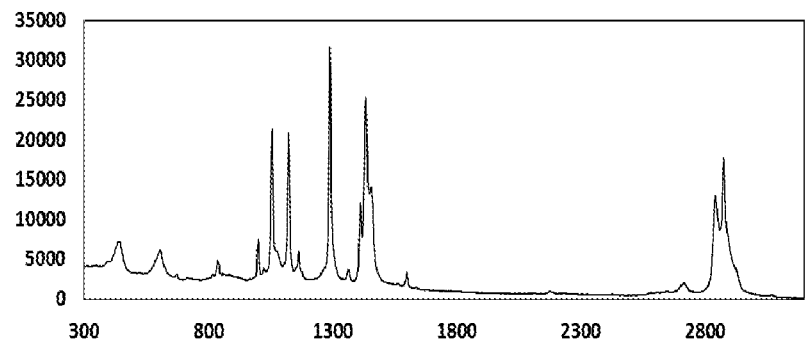
Figure 9C:
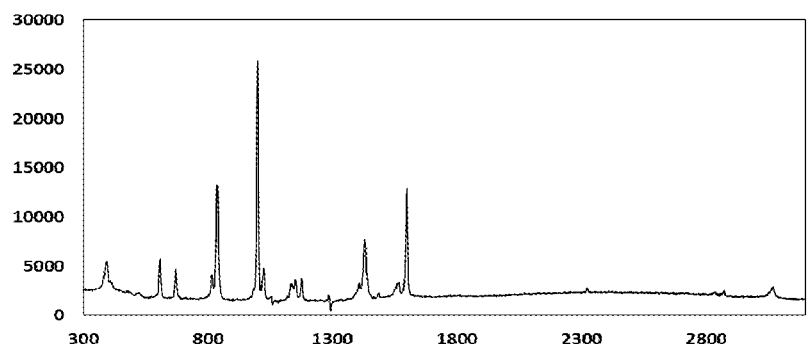
Figure 9D:
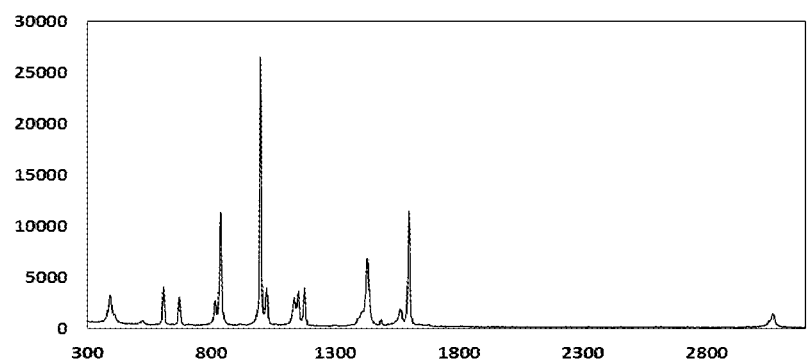

FIG. 9A shows the Raman spectrum of sodium benzoate powder contained in a white plastic bottle, which is measured with the aid of a light delivery and collection device as shown in FIG. 1A. FIG. 9B shows the measured Raman spectrum of the plastic bottle by removing the light delivery and collection device and focusing the laser beam directly on the surface of the plastic bottle. By properly scaling the spectrum in FIG. 9B and then subtracting the scaled spectrum from the spectrum in FIG. 9A, one can obtain a calculated Raman spectrum of the sodium benzoate powder as shown in FIG. 9C. Comparing this spectrum with the Raman spectrum shown in FIG. 9D, which is collected directly from purely sodium benzoate powder, it can be seen that the calculated spectrum is close enough to the spectrum of the pure sodium benzoate powder. By optimizing the mathematical algorithm of extracting the spectrum of the container, it is possible to further improve the quality of the obtained spectrum of the sample. Alternatively, mixture analysis can be performed directly using spectrum in FIG. 9A to identify the material makeup of the sample as a whole, including the container and the content inside.

Various mixture spectral analysis algorithms exist to accomplish such tasks. With prior knowledge of the container material, the chemical composition of the content inside can be determined. In yet another implementation, the container spectrum in FIG. 9B can be designated as a component, and a modified mixture analysis method can be used to identify the remaining components that make up the spectrum in FIG. 9A.

Figures 10A, 10B, 10C:
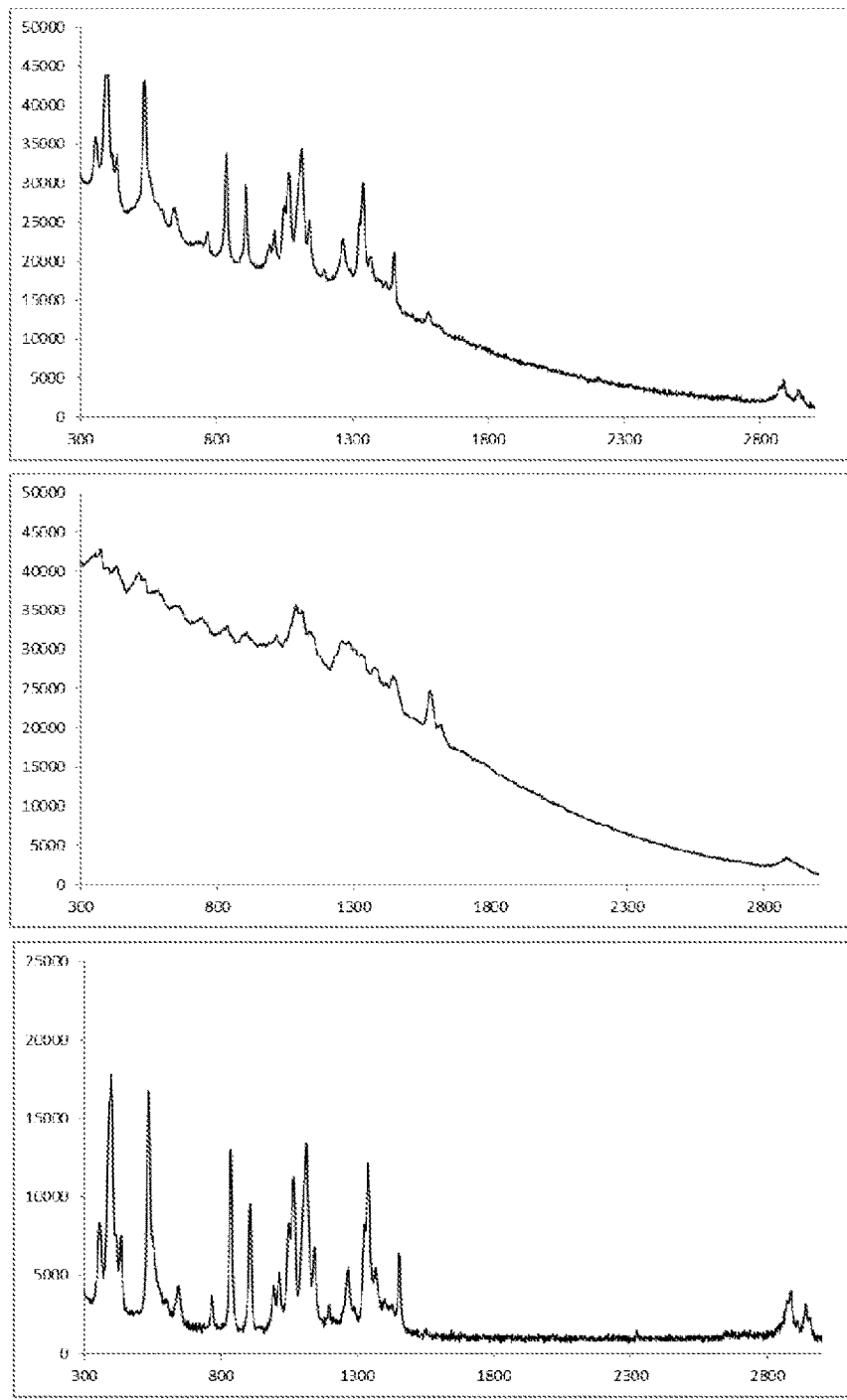
FIG. 10A-C shows the measured Raman spectrum of a D(+)-Glucose sample contained in a brown envelope, as well as the Raman spectrum of the brown envelope and the Raman spectrum of the D(+)-Glucose sample for comparison.

FIG. 10 illustrates how the light delivery and collection device enables material identification by means of Raman spectroscopy through a different kind of packaging material, i. e. a brown paper envelope. FIG. 10A shows the Raman spectrum of a D(+)-Glucose sample contained in the brown envelope, which is measured with the aid of a light delivery and collection device as shown in FIG. 1A. FIG. 10B shows the Raman spectrum obtained without the device and with the excitation beam focused on the brown envelope. FIG. 10C shows the Raman spectrum of the D(+)-Glucose sample measured in absence of the brown paper envelope. Here the brown envelope spectrum in FIG. 10B displays the signature of cellulose on top of a high level of fluorescence. The signature of the glucose content is almost completely absent. In contrast, the Raman spectrum obtained with the light delivery and collection device is almost entirely of D(+)-Glucose, with a relatively weak contribution from the cellulose. In this case, the material inside the packaging material can be directly identified by searching through a spectral library.

Figure 11A:
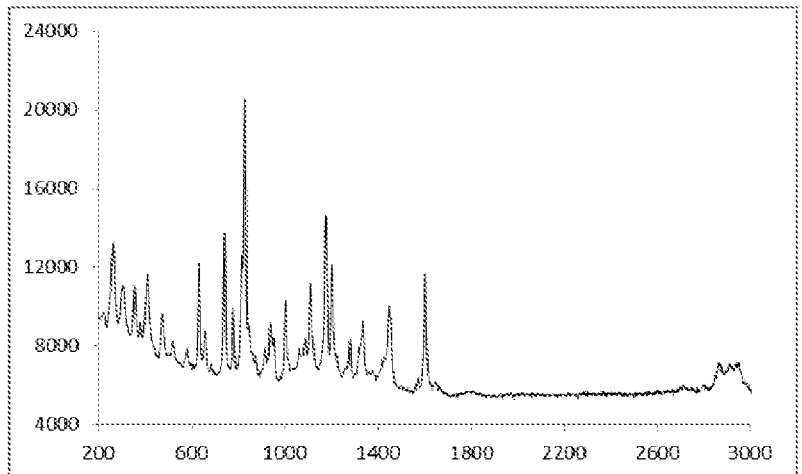
FIG. 11A-C shows the Raman spectrum of a coated ibuprofen tablet sample obtained in three different measurement modes.
Figure 11B:
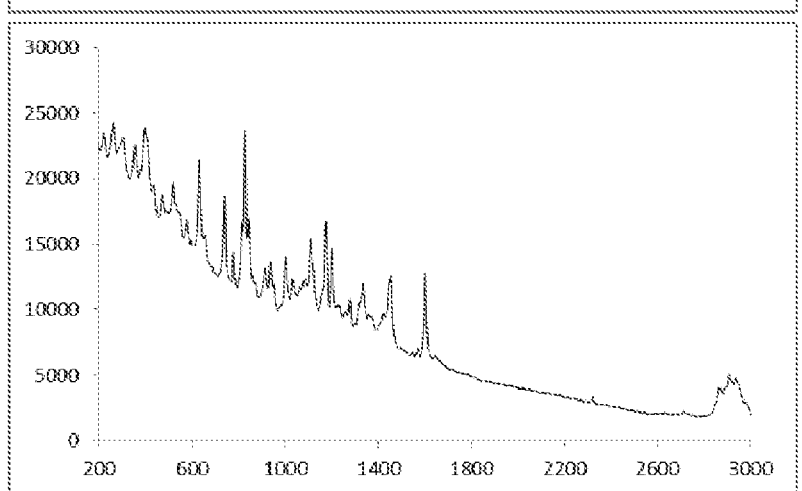
Figure 11C:
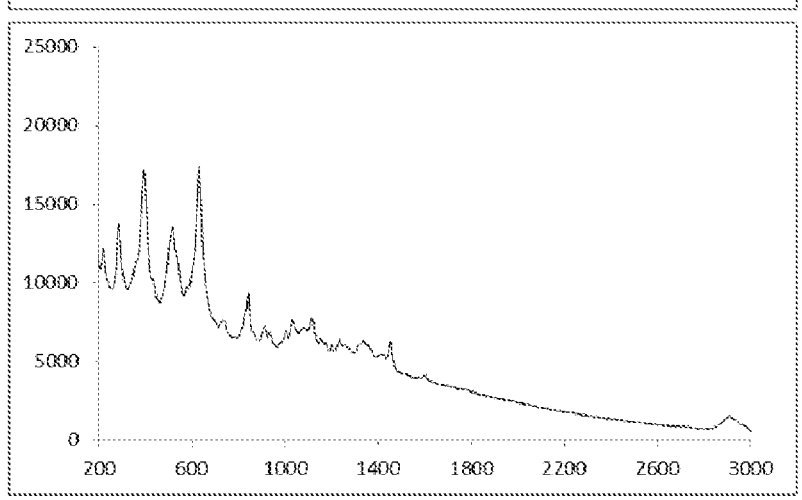

FIG. 11 illustrates how the light delivery and collection device used in transmission mode enables the measurement of bulk material property. Here the sample is an ibuprofen tablet (Advil, 200 mg) purchased from a local drug store. The tablet has a brown colored coating. The spectrum in FIG. 11A is obtained in transmission mode using the configuration shown in FIG. 4; the spectrum in FIG. 11B is obtained in reflection mode using the configuration shown in FIG. 1A; and the spectrum in FIG. 11C is obtained in reflection mode without the aid of the light delivery and collection device. The spectrum in FIG. 11C consists of features mostly from the coating of the tablet, while the transmissive Raman spectrum in FIG. 11A consists almost entirely of the drug material inside the coating. The spectrum in FIG. 11B is similar to the spectrum in FIG. 11A, but has relatively more contribution from the coating. To those skilled in the art, it is known that the transmission mode measures the Raman signal throughout the entire thickness of the sample, therefore is more advantageous when the bulk property of the sample as a whole is of interest.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An apparatus for performing spectroscopic analysis of a subject, the apparatus comprising:

a light source for producing excitation light at a first wavelength;

a reflective cavity with a specular reflective surface, the reflective cavity having a first aperture and a second aperture, the second aperture is configured to be applied to the subject such that the reflective cavity substantially forms an enclosure covering an area of the subject;

one or more optic components configured to focus the excitation light at the first aperture of the reflective cavity to deliver the excitation light into the reflective cavity, wherein the excitation light projects onto the second aperture of the reflective cavity and enters and interacts with the covered area of the subject and produces signal light at a second wavelength, wherein the reflective cavity reflects the excitation light and signal light which is reflected or back-scattered from the covered area of the subject and causes said reflected or back-scattered excitation light and signal light to re-enter the covered area of the subject at the second aperture of the reflective cavity, except said reflected or back-scattered excitation light and signal light that exits the reflective cavity through the first aperture of the reflective cavity, and wherein the first aperture is sized substantially just large enough to encompass the beam waist of the focused excitation light; and a spectrometer device for collecting and measuring an optical spectrum of the signal light.

2. The apparatus of claim 1, wherein the spectrometer device collects the signal light from the first aperture of the reflective cavity.

3. The apparatus of claim 1, wherein the reflective cavity is made of a material having high reflectivity to the excitation light and signal light.

4. The apparatus of claim 1, wherein the reflective cavity has a surface coating with high reflectivity to the excitation light and signal light.

5. The apparatus of claim 4, wherein the surface coating is a metal coating.

6. The apparatus of claim 4, wherein the surface coating is a dielectric coating.

7. The apparatus of claim 1, wherein the reflective cavity comprises at least one additional aperture.

8. The apparatus of claim 1, wherein the second aperture of the reflective cavity is at least two times as large as the first aperture of the reflective cavity in area.

9. The apparatus of claim 1, further comprising an optical window covering the second aperture of the reflective cavity, wherein the optical window is transparent to the excitation light and signal light.

10. The apparatus of claim 1, wherein the reflective cavity is formed by a solid optical material having a reflective coating.

11. The apparatus of claim 10, wherein the solid optical material has a spatially heterogeneous refractive index profile.

12. A method for performing spectroscopic analysis of a subject, the method comprising the steps of:

producing excitation light at a first wavelength;

providing a reflective cavity with a specular reflective surface, the reflective cavity having a first aperture and a second aperture;

applying the second aperture of the reflective cavity to the subject such that the reflective cavity substantially forms an enclosure covering an area of the subject;

providing one or more optic components configured to focus the excitation light at the first aperture of the reflective cavity to deliver the excitation light into the reflective cavity, wherein the excitation light is adapted to project onto the second aperture of the reflective cavity and enter and interact with the covered area of the subject and to produces a signal light at a second wavelength, wherein the reflective cavity reflects the excitation light and signal light which is reflected or back-scattered from the covered area of the subject and causes said reflected or back-scattered excitation light and signal light to re-enter the covered area of the subject at the second aperture of the reflective cavity, except said reflected or back-scattered excitation light and signal light that exits the reflective cavity through the first aperture of the reflective cavity, and wherein the first aperture is sized substantially just large enough to encompass the beam waist of the focused excitation light; and measuring an optical spectrum of the signal light.

13. The method of claim 12, wherein the reflective cavity is made of a material having high reflectivity to the excitation light and signal light.

14. The method of claim 12, wherein the reflective cavity has a surface coating with high reflectivity to the excitation light and signal light.

15. The method of claim 14, wherein the surface coating is a metal coating.

16. The method of claim 14, wherein the surface coating is a dielectric coating.

17. The method of claim 12, wherein the second aperture of the reflective cavity is at least two times as large as the first aperture of the reflective cavity in area.

18. The method of claim 12, wherein the reflective cavity is formed by a solid optical material having a reflective coating.

19. The method of claim 18, wherein the solid optical material has a spatially heterogeneous refractive index profile.

20. A method for performing spectroscopic analysis of a subject, the method comprising the steps of:

producing excitation light at a first wavelength;

delivering the excitation light to a first side of the subject and causing the excitation light to enter and interact with the subject to produce signal light at a second wavelength, wherein the excitation light and signal light at least partially transmits from the first side to a second side opposite to the first side of the subject;

providing a reflective cavity with a specular reflective surface, the reflective cavity having a first aperture and a second aperture;

applying the second aperture of the reflective cavity to the second side the subject such that the reflective cavity substantially forms an enclosure covering an area on the second side of the subject, wherein the reflective cavity reflects said transmitted excitation light and signal light and causes said transmitted excitation light and signal light to re-enter the covered area of the subject at the second aperture of the reflective cavity, except said transmitted excitation light and signal light that exits the reflective cavity through the first aperture of the reflective cavity, and wherein the first aperture is sized substantially just large enough to encompass the beam waist of the excitation light; and measuring an optical spectrum of the signal light emitted from the first aperture of the reflective cavity.

21. A method for performing spectroscopic analysis of a subject having a surface layer and a sub-surface layer of different materials, the method comprising the steps of:

producing excitation light;

providing a reflective cavity with a specular reflective surface, the reflective cavity having a first aperture and a second aperture;

applying the second aperture of the reflective cavity to the subject such that the reflective cavity substantially forms an enclosure covering an area of the subject;

delivering the excitation light through the first aperture to be projected onto the second aperture of the reflective cavity and causing the excitation light to enter and interact with the covered area of the subject to produce a first signal light, wherein the reflective cavity reflects the excitation light and first signal light which is reflected or back-scattered from the covered area of the subject and causes said reflected or back-scattered excitation light and first signal light to re-enter the covered area of the subject at the second aperture of the reflective cavity, except said reflected or back-scattered excitation light and first signal light that exits the reflective cavity through the first aperture of the reflective cavity, and wherein the first aperture is sized substantially just large enough to encompass the beam waist of the excitation light;

measuring the first signal light to obtain a first optical spectrum of the subject which contains information of both the surface layer and the sub-surface layer of the subject;

removing the reflective cavity and focusing the excitation light to the surface layer of the subject to excite a second signal light from the subject, and measuring the second signal light to obtain a second optical spectrum of the subject which mainly contains information of the surface layer of the subject; and analyzing a difference between the first optical spectrum and the second optical spectrum to identify the material of the sub-surface layer.

\* \* \* \* \*